(12) United States Patent
Kim et al.

(10) Patent No.: US 9,857,363 B2
(45) Date of Patent: Jan. 2, 2018

(54) MEMBRANE SENSOR CAPABLE OF SEQUENTIALLY CHANGING REACTION CONDITION BY SINGLE SAMPLE INJECTION

(71) Applicant: INGIBIO, LTD., Gwangju (KR)

(72) Inventors: Min-Gon Kim, Gwangju (KR); Hyou-Arm Joung, Gwangju (KR); Jun-Hyoung Ahn, Daejeon (KR)

(73) Assignee: INGIBIO, LTD., Gwangju (KR)

( * ) Notice: Subject to any disclaimer, the term of this patent is extended or adjusted under 35 U.S.C. 154(b) by 207 days.

(21) Appl. No.: 14/349,932

(22) PCT Filed: Oct. 5, 2012

(86) PCT No.: PCT/KR2012/008085
§ 371 (c)(1),
(2) Date: Apr. 4, 2014

(87) PCT Pub. No.: WO2013/051889
PCT Pub. Date: Apr. 11, 2013

(65) Prior Publication Data
US 2014/0255958 A1 Sep. 11, 2014

(30) Foreign Application Priority Data

Oct. 6, 2011 (KR) .......... 10-2011-0101670
Oct. 5, 2012 (KR) .......... 10-2012-0110523

(51) Int. Cl.
*G01N 33/543* (2006.01)
*G01N 33/544* (2006.01)
*G01N 33/558* (2006.01)

(52) U.S. Cl.
CPC ..... *G01N 33/54306* (2013.01); *G01N 33/544* (2013.01); *G01N 33/558* (2013.01)

(58) Field of Classification Search
None
See application file for complete search history.

(56) References Cited

U.S. PATENT DOCUMENTS

| | | | | |
|---|---|---|---|---|
| 5,166,051 A | * | 11/1992 | Killeen | G01N 33/521 422/401 |
| 5,968,765 A | * | 10/1999 | Grage et al. | 435/25 |
| 7,494,818 B1 | | 2/2009 | Anaokar et al. | |
| 2004/0235182 A1 | * | 11/2004 | Jones | G01N 33/543 436/71 |

(Continued)

FOREIGN PATENT DOCUMENTS

| | | |
|---|---|---|
| CN | 101035429 A | 9/2007 |
| EP | 0407800 A2 * | 6/1990 |

(Continued)

OTHER PUBLICATIONS

Chinese Office Action dated Mar. 16, 2015.

(Continued)

*Primary Examiner* — Rebecca L Martinez
(74) *Attorney, Agent, or Firm* — Hauptman Ham, LLP

(57) ABSTRACT

Disclosed herein are a membrane sensor capable of changing a reaction condition by a single sample injection and a method for measuring a reaction using the same, and more specifically, a membrane sensor designed so that a bio reaction having two or more reaction conditions is sequentially generated by a single sample injection, by forming an asymmetric membrane between a reactant storing part and a reaction membrane.

17 Claims, 6 Drawing Sheets

(56) References Cited

U.S. PATENT DOCUMENTS

| | | |
|---|---|---|
| 2005/0214161 A1 | 9/2005 | Gupta |
| 2006/0062688 A1* | 3/2006 | Lawrence .............. G01N 21/78 422/400 |
| 2007/0135698 A1 | 6/2007 | Shah et al. |
| 2007/0202611 A1* | 8/2007 | Shimizu ................ B01L 3/5023 436/522 |
| 2008/0241913 A1* | 10/2008 | Horisaka et al. .......... 435/287.9 |
| 2009/0142781 A1 | 6/2009 | Shimizu et al. |
| 2010/0233708 A1* | 9/2010 | Mehra et al. ..................... 435/6 |

FOREIGN PATENT DOCUMENTS

| | | |
|---|---|---|
| EP | 1965212 A1 | 9/2008 |
| JP | 2006507511 A | 3/2006 |
| JP | 2006524815 A | 11/2006 |
| KR | 20010106902 A | 12/2001 |
| KR | 100348351 B1 | 8/2002 |
| KR | 100591300 B1 | 6/2006 |
| KR | 100599420 B1 | 7/2006 |

OTHER PUBLICATIONS

Hyou-Arm Joung et al., "An automatic enzyme immunoassay based on a chemiluminescent lateral flow immunosensor", Biosensors and Bioelectronics, Oct. 16, 2013, pp. 330-335, vol. 53, Elsevier B.V., available on line.
European Search Report dated May 20, 2015 in connection with the counterpart European Patent Application No. 12837916.1.
International Search Report for PCT/KR2012/008085 dated Mar. 26, 2013.

* cited by examiner

3 MINUTES ELAPSED    5 MINUTES ELAPSED

10 MINUTES ELAPSED   15 MINUTES ELAPSED

MEMBRANE SENSOR CAPABLE OF SEQUENTIALLY CHANGING REACTION CONDITION BY SINGLE SAMPLE INJECTION

TECHNICAL FIELD

The present invention relates to a membrane sensor capable of changing a reaction condition by a single sample injection, and a method for measuring a reaction using the same, and more specifically, to a membrane sensor designed so that a bio reaction having two or more reaction conditions is sequentially generated by a single sample injection, by forming an asymmetric film between a reactant storing part and a reaction membrane.

BACKGROUND ART

A lateral flow assay (LFA) system is mainly used as a method for rapidly measuring an antigen-antibody reaction. It is general in the LFA that an antibody is fixed to a membrane in which a liquid sample enables to flow due to a capillary phenomenon, wherein the membrane has a conjugate pad and a sample pad connected on an upper portion thereof and an absorption pad connected on a lower portion thereof. The conjugation pad contains a dried gold nanoparticle conjugate to which an antibody capable of selectively binding to a sample material is fixed. In the membrane, materials capable of binding an antibody selectively reacting with the sample material and capable of binding the antibody fixed to the gold nanoparticle are fixed at different positions, respectively. The antibody fixed to the membrane and the antibody fixed to the gold nanoparticle, which are capable of selectively binding the sample material, are configured so as to bind to each other in a sandwich shape with respect to the sample material. The absorption pad consists of a material capable of favorably absorbing the liquid sample. In the case where a liquid sample solution drops onto a sample pad in the above-mentioned LFA system, when a sample is present, antibodies having selectivity on the sample, that is, antibodies fixed to the gold nanoparticle and the membrane are bound to each other in a sandwich shape, thereby forming a band capable of confirming with the naked eye at a position of the membrane having the antibodies fixed thereto.

As a membrane sensor, there are various published documents such as Korean Patent No. 599420 entitled with Membrane Strip Biosensor System for Point-of-CareTesting; Japanese Patent Laid-Open Publication No. 2006-507511 entitled with Composite Sensor Membrane; Korean Patent No. 348351 entitled with Electrochemical Membrane Strip Biosensor; U.S. Pat. No. 7,494,818 entitled with Method for Determining Concentration of Multiple Analytes in a Single Fluid Sample; Korean Patent No. 591390 entitled with Sensor Having Membrane and Method For Manufacturing the Same; US Patent Application Publication No. 2005-214161 entitled with Test Device for Simultaneous Measurement of Multiple Analytes in a Single Sample, and the like.

However, the existing LFA system using nanoparticles requires improving a detection sensitivity due to a low detection sensitivity of 1 ng/ml and has a disadvantage in that it is difficult to implement a high sensitivity reaction such as enzymatic color reaction, fluorescence, chemiluminescence, and the like, except for a sandwich method using nanoparticles, by one-step sample injection. In addition, in the case of a bio reaction required for two or more stages of reaction conditions such as an enzyme reaction and a chemiluminescent reaction, an LFA strip has a difficulty in obtaining a desired result by a single sample injection, and in a case of a chemiluminescent strip, 2 step method in which a luminol reaction solution is secondarily injected for a luminol reaction after an antigen-antibody reaction is primarily achieved, or a technology of positioning a support having a luminol reactant applied onto a reaction membrane and being contact the support with a reactant part at a time of completion of an antigen-antibody reaction (EP No. 1,9652,212 and US Patent Application No. 2009-142781) have been known so far.

Therefore, development of a strip capable of measuring a bio reaction having two or more stages of reaction conditions by one-step process through a single sample injection has been demanded.

DISCLOSURE

Technical Problem

An object of the present invention is to provide a biosensor capable of easily implementing a bio reaction or a chemical reaction having two or more reaction conditions by a single detection sample injection in a lateral flow assay (LFA) strip.

Technical Solution

In order to achieve the object of the present invention, according to an exemplary embodiment of the present invention, there is provided a membrane strip biosensor using a lateral flow including: a reaction membrane; an asymmetric membrane positioned on the reaction membrane; and a reactant storing part positioned on the asymmetric membrane and treated with a reactant.

The reaction membrane may have a sample pad positioned at any one of both ends thereof and an absorption pad positioned at the other of both ends thereof.

The asymmetric membrane may have an average pore size of 0.01 to 50 µm and may be made of one or more kinds selected from polysulfone, polyethersulfone and polycarbonate.

The reaction membrane may be made of one or more kinds selected from nitrocellulose, nylon, polysulfone, polyethersulfone, and polyvinylidene fluoride (PVDF).

A biomaterial capable of capturing an analysis target material in an injected sample may be treated on the reaction membrane.

A first reactant reacting with an analysis target material may be treated on the reaction membrane, and a second reactant generating a signal may be treated in the reactant storing part.

The membrane strip biosensor may further include a conjugation pad positioned so as to be adjacent to the sample pad, a first reactant reacting with an analysis target material may be treated on the conjugation pad, and a second reactant generating a signal may be treated in the reactant storing part.

The first reactant may be one or two or more kinds of conjugates selected from antibodies, antigens, enzymes, peptides, proteins, DNAs, RNAs, peptide nucleic acids (PNAs), aptamers and nanoparticles, and the second reactant may be one or more kinds selected from light absorbing materials, fluorescent materials, luminescent materials, electrochemical signal generating materials and signal amplifying materials amplifying intensity of light absorption signal, fluorescent signal, luminescent signal and electrochemical signal.

According to another exemplary embodiment of the present invention, there is provided a method for analyzing a bio sample including: measuring an analysis target material by injecting the sample into the membrane strip biosensor as described above.

Advantageous Effects

With the biosensor according to the present invention, since the enzyme reaction, the antigen-antibody reaction, the chemical reaction, and the like, having two or more reaction conditions, may be implemented by a single detection sample injection, the applicable range of the existing LFA strip sensor having high detection sensitivity may be more increased.

[Detailed Description of Main Elements]

| | |
|---|---|
| 11: Sample Pad | 12: Absorption Pad |
| 13: Conjugation Pad | 14: Reactant Storing Part |
| 15: Asymmetric membrane | 16: Reaction Membrane |
| 17: Lower Substrate | 20: Anti-CRP Antibody-Peroxidase Complex |
| 21: Anti-CRP Polyclonal Antibody | |
| 22: Anti-Mouse IgG | 23: Choline Oxidase |

BEST MODE

The present invention relates to a membrane biosensor including an asymmetric membrane between a reactant storing part and a reaction membrane.

Figure 1:
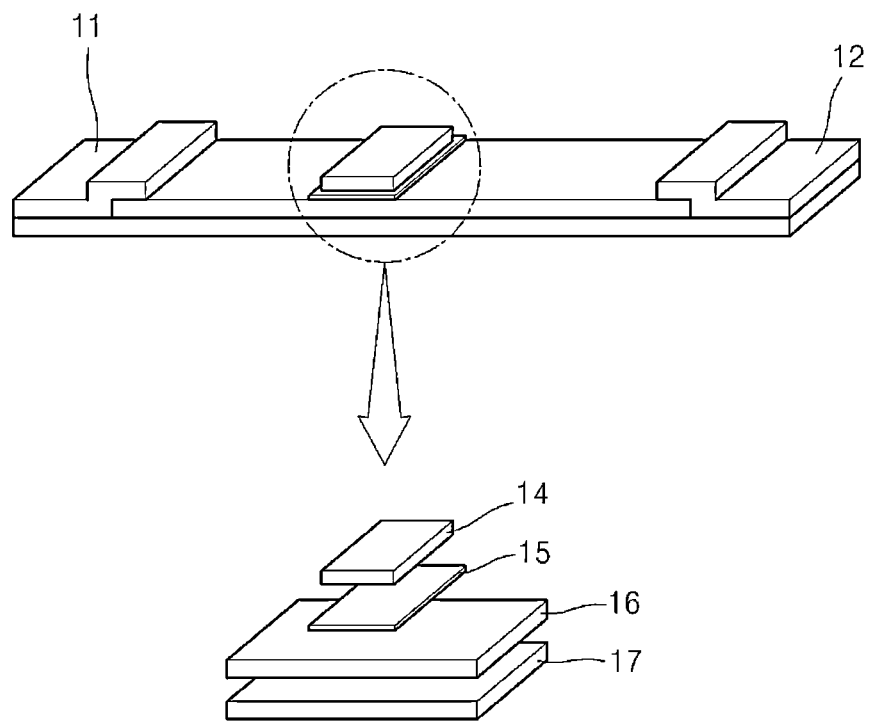
FIGS. 1 and 2 show a configuration of a membrane sensor according to an embodiment of the present invention.

FIG. 1 shows a basic configuration of a membrane sensor according to an embodiment of the present invention.

As shown in FIG. 1, the strip biosensor includes a reactant storing part 14, an asymmetric membrane 15, a reaction membrane 16, and a lower substrate 17, and includes a sample pad 11 and an absorption pad 12 which are basic components of a lateral flow assay (LFA) strip.

The reactant storing part 14, which is to store reactants required for a second reaction induced after a first reaction is performed by an initially injected sample and a predetermined time elapses, may store a bio sample, a chemical sample, a reaction condition regulating material, and the like. In the reactant storing part 14, all materials capable of treating the reactant in an aqueous solution state and being dried may be used. The reactant storing part 14 may include an absorption pad, a membrane, and the like, generally used in the strip sensor, and is preferably made of materials such as cellulose, polyester, polypropylene, or glass fiber.

The asymmetric membrane 15, which is a film in a structure in which a large pore part and a small pore part are asymmetrically disposed, has different pore size between an upper surface and a lower surface thereof, wherein the large pore part is in contact with the reactant storing part 14 and the small pore part is in contact with the reaction membrane 16. Therefore, during lateral flow of an injected liquid sample through the reaction membrane 16, the initially injected sample in flow is allowed to be diffused, and after diffusion is completed, the reactant dried in the reactant storing part 14 is transferred toward the reaction membrane 16 but the injected sample flowing through the reaction membrane 16 is prevented from being transferred toward the reactant storing part 14. The asymmetric membrane 15 has an average pore size of 0.01 to 50 μm, and preferably, 1 to 30 μm.

It is general that an aqueous liquid has a property in that it favorably flows from a large pore part to a small pore part but has a difficulty in flowing in an opposite direction thereto, which may be explained by a capillary phenomenon. Therefore, a general fluid flows through a porous membrane having a hydrophilic property, and in the asymmetric membrane 15 having an asymmetric porous structure, a vertical flow is first achieved from a large pore part to a small pore part, and the lateral flow is then achieved.

As a result, during a lateral flow of the injected aqueous sample through the reaction membrane 16, the asymmetric membrane 15 in a dried state serves as an inter medium allowing the aqueous sample to diffuse toward the reactant storing part 14 and after the diffusion of all aqueous samples is completed to sufficiently soak the reactant storing part 14, the reaction membrane 16 in contact with the small pore part prevents the injected sample from being diffused into the reactant storing part 14 any more. At the same time, the injected sample flows in a lateral direction through the reaction membrane 16, and after a predetermined time elapses, the reactant present in the reactant storing part 14 slows flows out through the asymmetric membrane 15 toward the reaction membrane 16, such that reaction conditions of the strip sensor may be changed depending on properties of materials stored in the reactant storing part 14. That is, due to the presence of the asymmetric membrane 15, time required that the reactant flows out is delayed and the reactant flowing out through the reactant storing part 14 toward the reaction membrane 16 may be regulated so as to uniformly flow from the reaction membrane 16 to the absorption pad 12 for a predetermined time, and by including acid, base, and buffer composition rather than the reactant, pH control and change in reaction conditions of the reaction membrane 16 may be achieved.

The asymmetric membrane 15 is made of a hydrophilic material and has non-uniform pores therein, and as long as the large pore part and the small pore part may be divided into the film, the asymmetric membrane 15 is not limited in view of a kind, but is preferably made of a material selected from polysulfone, polyethersulfone and polycarbonate.

In addition, the reaction membrane 16 serves as a passage through which bio samples transfer and includes all materials having a membrane shape and capable of performing a lateral flow and confirming chemical and biological reaction results. More preferably, a membrane made of a material selected from nitrocellulose, nylon, polysulfone, polyethersulfone, and polyvinylidene fluoride (PVDF) is preferably used; however, the present invention is not limited thereto but any material among materials capable of performing a lateral flow of a liquid sample may be appropriately selected by a person skilled in the art.

In the present invention, the sample pad 11 allows the injected liquid sample to be developed into the reaction membrane, and the absorption pad 12 absorbs the sample developed into the reaction membrane. The sample pad or the absorption pad is not limited in view of a kind thereof as long as a material is capable of absorbing the liquid sample; however, is preferably made of a material such as cellulose, polyester, polypropylene, or glass fiber.

Figure 2:
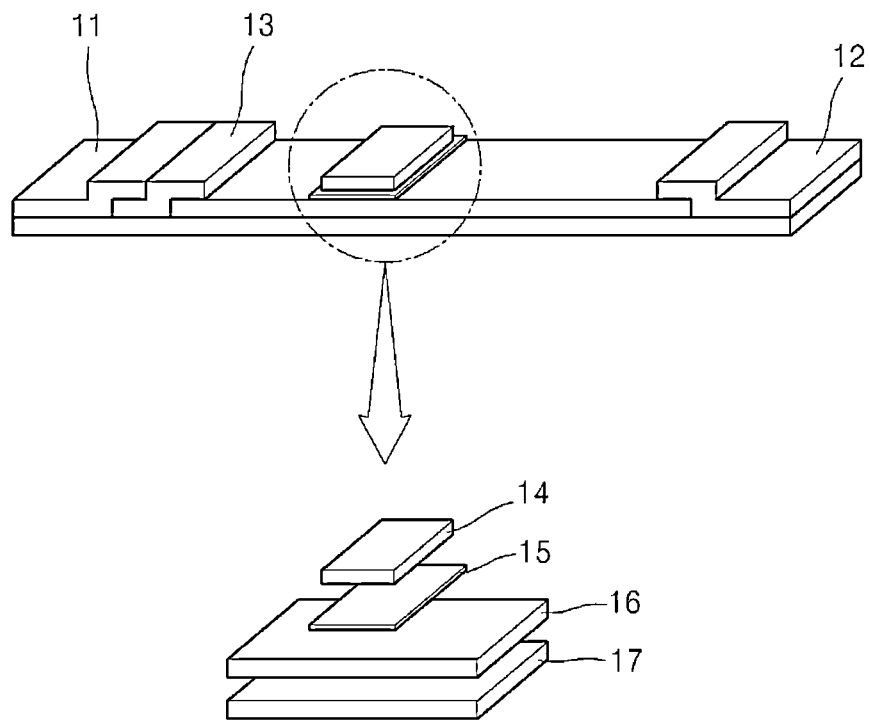

FIG. 2 shows a basic configuration of a strip biosensor according to an embodiment of the present invention, and the strip biosensor further includes a conjugation pad 13. The conjugation pad 13 may be used by applying a first reactant capable of selectively binding to an analysis target material thereon and performing a drying process. As the first reactant, one or two or more kinds of conjugates selected from antibodies, antigens, enzymes, pepsides, proteins, DNAs, RNAs, peptide nucleic acids (PNAs), aptamers and nanoparticles, may be used.

Meanwhile, in the case where the first reactant is a metal nanoparticle, the analysis target material may be detected through a color change of the material nanoparticle due to a selective reaction between a receptor and the analysis target material, and the analysis target material may be quantitatively analyzed by measuring absorbance, electrical conductivity, and the like, of a complex of the analysis target material selectively bound to the receptor on the membrane and the metal nanoparticle. The metal nanoparticle is, for example, a gold nanoparticle, a silver nanoparticle, a copper nanoparticle, and the like, but the present invention is not limited thereto.

In the case where the first reactant is an enzyme, an enzyme substrate or an enzyme reaction product, due to the selective reaction between the receptor and the analysis target material, the analysis target material or the receptor reacts with the enzyme, the enzyme substrate or the enzyme reaction product to generate an enzyme reaction such as an oxidation-reduction reaction, or the like, wherein the analysis target material may be detected by measuring light absorption, fluorescence, luminescence, or the like, of the product due to the enzyme reaction. The enzyme may be glucose oxidase, glucose dehydrogenase, alkaline phosphatase, peroxidase, and the like, but the present invention is not limited thereto, and the enzyme substance may be glucose, hydrogen peroxide, and the like, but the present invention is not limited thereto.

In addition, the second reactant generating a signal may be treated in the reactant storing part, and as the second reactant, light absorbing materials, fluorescent materials, luminescent materials, electrochemical signal generating materials signal amplifying materials amplifying intensity of light absorption signal, fluorescent signal, luminescent signal and electrochemical signal, may be included, and more specifically, chemiluminescent materials such as luminol, lumigen, and luciferin, electrochemiluminescent materials such as ruthenium tris-bipyridine(Ru(Bpy)3), and the like, enzyme color substances such as 3,3',5,5'-tetramethylbenzidine(TMB), 3,3'-diaminobenzidine tetrahydrochloride (DBA), 2,2'-azino-bis(3-ethylbenzthiazoline-6-sulphonic acid) (ABTA), 4-chloro-1-naphthol(CN), BCIP (5-bromo-4-chloro-3-indolyl-phosphate)/NBT (nitroblue tetrazolium), and the like, fluorescent materials such as organic fluorescent materials (for example, FITC, Rhodamine Green, thiadicarbocyanine, Cy2, Cy3, Cy5, Alexa 488, Alexa 546, Alexa 594 and Alexa 647), quantum dot, and the like, metal nanoparticles, magnetic nanoparticles, pH adjuster (for example, NaOH, HCl, a buffer), and the like, may be used, and signal amplifying materials, signal inhibitors, and the like, may be used with together.

In addition, the bio material (receptor) capable of capturing the analysis target material in the injected sample is treated on the reaction membrane 16.

As a result, in the case where the first reactant is applied and dried onto the conjugation pad 13, reactions by the first reactant and the second reactant are sequentially generated, such that the analysis target material in the sample may be measured by a signal of a signal generating material, and the asymmetric membrane 15 delays a release time of the second reactant.

In the present invention, as the conjugation pad 13, all materials may be used as long as the reactant is easily detached from the conjugation pad in a case where the first reactant is applied and dried onto the conjugation pad 13 and then the conjugation pad is soaked in a liquid, or any conjugation pad may be used as long as the conjugation pad is generally used in the LFA system, and all membrane materials such as nitrocellulose, nylon, polysulfone, polyethersulfone, or polyvinylidene fluoride (PVDF) as well as materials such as cellulose, polyester, polypropylene, or glass fiber, may be used.

The sample injected through the sample pad in the present invention may be any samples containing or not containing the analysis target material, and indicates a fluid capable of flowing from the sample pad to the absorption pad, having the reaction membrane as a medium. Specifically, the sample indicates a liquid sample containing blood, serum, or specific analytes (DNA, proteins, chemicals, toxins, and the like).

The biosensor of the present invention may be implemented as various strip sensors depending on the specific analytes in the sample. For example, when detecting a specific protein in a serum, an antibody capable of selectively binding a specific material is fixed between the reactant storing part and the absorption pad, and when a serum is injected into the sample pad, using a detection antibody-enzyme complex, a sandwich immune reaction is achieved, and the enzyme of the detection antibody and a reactant showing a specific signal are contained in the reactant storing part, such that an initial antigen-antibody reaction is achieved, thereby implementing a sensor capable of showing a specific signal. In particular, in a case where reaction conditions of materials positioned at the reactant storing part and antigen-antibody reaction conditions are different, or a cross reaction occurs or a non-specific reaction occurs, it is difficult to implement one-step process in a general LFA strip sensor; however, the one-step process may be easily implemented in the biosensor of the present invention.

The one-step process indicates that reaction and measurement are completed by performing a single sample injection. For example, in a case of a chemiluminescent immune sensor using luminol, luminescent reaction of the luminol has the maximum value at pH 9 or more, which is different from pH condition at which an antigen-antibody binding or an enzyme reaction has the maximum value, and at neutral pH or lower than that, There is a problem in that precipitation of the luminol occurs. In a general biosensor, in most cases, the injected sample such as blood or serum has neutral pH, such that it is significantly difficult to perform the luminol reaction by one-step process. However, as described in the following Examples, the biosensor of the present invention may easily implement one-step process even in a case having two or more reaction conditions, such that a usage range of the LFA strip sensor may be widen.

Meanwhile, the present invention provides a method for measuring an analysis target material through an immune reaction or an enzyme reaction by injecting a sample into the membrane strip biosensor.

Depending on reaction of a measured target, kinds of the reactants and treatment of the reaction membrane, and the like, may be regulated; however, as one example thereof, in a case of a chemiluminescent immune strip sensor, a detection antibody is stored in the conjugation pad, a capturing antibody and a second antibody are fixed to the reaction membrane, and a sample is injected in a state in which a material generating a luminescent reaction is contained in the reactant storing part, thereby confirming a reaction degree. In addition, even in a case not including the conjugation pad, a desired result may be deduced by treating the detection antibody in the reaction membrane.

In the reaction, when being treated with the reaction membrane, general bio materials, in particular, proteins, are absorbed and fixed to the reaction membrane; however, when being treated with surfactant or a soluble polymer, general bio materials flow with the injected sample while the injected sample is transferred along the reaction membrane. Here, as the surfactant, Surfactant 10G, and the like, may be used, and as the soluble polymer, polyvinylpyrrolidone (PVP) polymer having a weight average molecular weight of 1,000 to 100,000 g/mole, may be used, but the present invention is not limited thereto.

The above-described embodiments and additional embodiments of the present invention will be specifically described through desired Examples to be described below with reference to the accompanying drawings. Hereinafter, embodiments of the present invention will be described in detail so that the present invention may be easily understood and practiced by those skilled in the art.

However, the following examples are only for exemplifying the present invention, and it will be obvious to those skilled in the art that the scope of the present invention is not construed to be limited to these examples.

EXAMPLE 1

Strip Sensor Capable of Sequentially Changing pH by Single Sample Injection

A sodium carbonate (20 μL, 50 mM) buffer at pH 9.0 was treated in a reactant storing part (4 mm×4 mm) made of a glass fiber and dried. Then, a dried nitrocellulose membrane (Millipore, 180 sec Nitrocellulose, 4 mm×25 mm) obtained by treating 0.05 wt % of α-naphtolbenzein (10 μL in 1% surfactant 10G) and 50 wt % of ethanol was used as a reaction membrane. The α-naphtolbenzein, which is a pH indicator reagent, has a property that color thereof is changed from yellow to blue depending on pH change in 8 to 9.

In addition, as an asymmetric membrane, a film for separating serum (Vivid™, Pall, 4 mm×4 mm, an average pore size in a large pore part: about 10 μm, an average pore size in a small pore part: about 0.1 μm) made of polysulfone was used, and as a sample pad (4 mm×10 mm) and an absorption pad (4 mm×20 mm), a glass fiber material was used, thereby configuring a biosensor as shown in FIG. 1.

Figure 3:
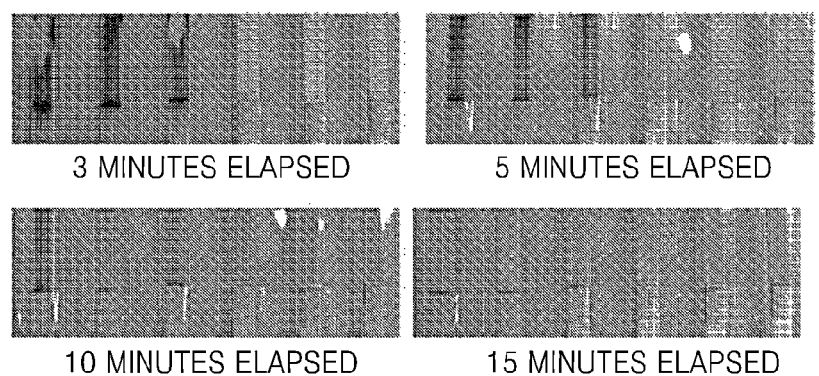
FIG. 3 shows a photograph showing a color change depending on a pH change of reaction membranes depending on time passage between Example 1 and Comparative Example 1; Here, three membranes on the left side among all six membranes indicate Comparative Examples, and three membranes on the right side indicate Examples.
Figure 4:
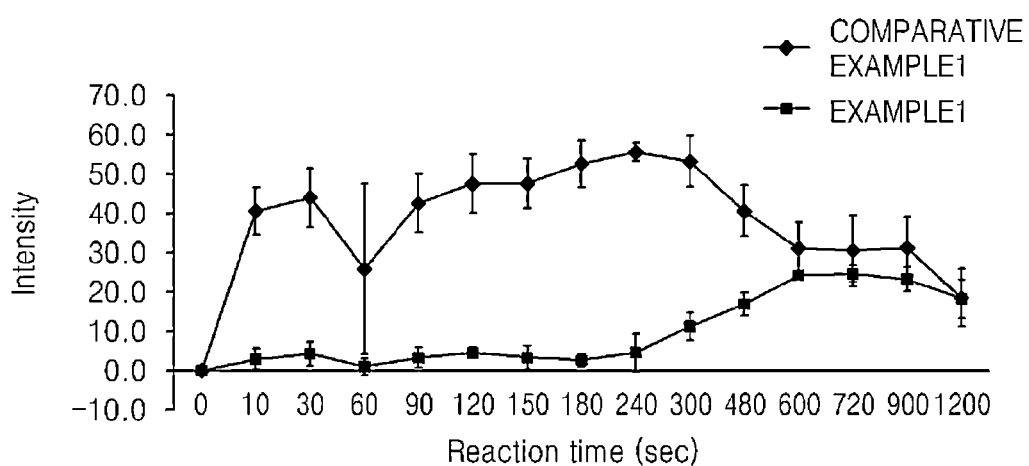
FIG. 4 is a graph showing comparison of color intensity measured depending on time passage between Example 1 and Comparative Example 1.

60 μL of PBS buffer (pH 7.4) was injected into the sample pad and a degree at which a sodium carbonate buffer at pH 9.0 of the reactant storing part flows into the reaction membrane is measured through color change between the reactant storing part and the absorption pad depending on time, and results thereof are shown in FIG. 3. A color of the reaction membrane indicates an amount at which the sodium carbonate buffer component of the reactant storing part flows. In addition, intensity of the color was measured depending on time and shown in FIG. 4.

It was confirmed from FIG. 3 that a color change was not shown at all within 5 minutes after the PBS buffer was injected, but after 5 minutes elapsed from the injection, the sodium carbonate buffer slowly and uniformly flowed out. It may be appreciated that the asymmetric membrane could delay the reaction solution of the reactant storing part from flowing out for about 5 minutes after the PBS buffer was injected, and could regulate the reactant to flow out at a predetermined concentration for about 5 to 15 minutes.

COMPARATIVE EXAMPLE 1

Strip Sensor not Including Asymmetric Membrane

Comparative Example 1 was conducted by injecting a PBS buffer into a sample pad as the same as Example 1 above except for not including the asymmetric membrane in Example 1 above, a color change depending on time was observed, and results thereof were shown in FIG. 3.

It was confirmed from FIG. 3 that after 10 seconds elapsed from the injection of the PBS buffer, the color was deeply and non-uniformly changed, which means that in a case of not including the asymmetric membrane, the reaction solution non-uniformly flowed out.

EXAMPLE 2

Chemiluminescent Strip Sensor Capable of Measuring C-Reactive Protein (CRP) in Human Serum by Single Sample Injection (Including Conjugation Pad)

Figure 5:
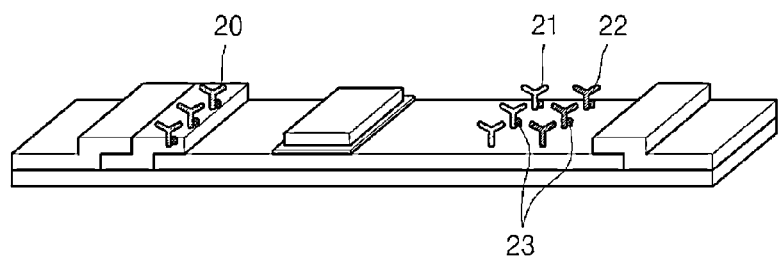
FIG. 5 shows a configuration of a chemiluminescent membrane sensor in Example 2.

As shown in FIG. 5, a strip designed so as to apply an object of the present invention to an antigen-antibody chemiluminescent reaction was fabricated, Unlike Example 1 above, a conjugation pad (fusion 5, whatman, 4 mm×10 mm) was fabricated, and 0.2 μg (Abcam) of an anti-CRP antibody-peroxidase complex 20 pretreated with 100 μg of Surfactant 10G and 200 μg of PVP 55K was added thereto. In addition, 140 μg of luminol and 58 μg of choline chloride were treated in the reactant storing part.

Then, a mixture of 0.8 μg/mL of an anti-CRP polyclonal antibody 21 and 0.1 U/mL of choline oxidase 23 was fixed to a side close to the reactant storing part between the reactant storing part and the absorption pad and a mixture of a 0.8 μg/mL of anti-mouse IgG 22 and 0.1 U/mL of choline oxidase 23 was fixed to a side close to the absorption pad. Here, each fixation was treated with a dispenser and dried.

Figure 6:
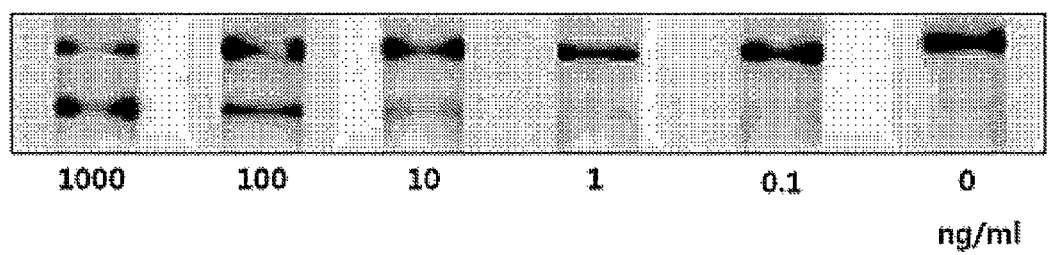
FIG. 6 is a photograph showing results measured for a concentration of C-reactive protein (CRP) in a human serum in Example 2.

In a case where 90 µL of serum was injected into the sample pad, the CRP antigen in the serum was passed through the sample pad and reacted with the detection antibody-peroxidase complex of the conjugation pad and transferred through the reaction membrane, and when being in contact with a capturing antibody, the CRP antigen was reacted with the capturing antibody due to a sandwich antigen-antibody reaction. The detection antibody-peroxidase complex which was not reacted was bound to anti-mouse IgG. After 5 minutes, luminol and choline chloride present in the reactant storing part flowed through the reaction membrane, and choline oxidase and choline chloride in each initial region to which each antibody was fixed were reacted with together, producing hydrogen peroxide. In a case where the detection antibody-peroxidase complex was present, the produced hydrogen peroxide was decomposed to generate a luminol luminescent reaction. A picture measured depending on a concentration of CRP in the injected serum was shown in FIG. 6, and it was confirmed from FIG. 6 that detection was achieved up to a concentration of 0.1 ng/ml.

EXAMPLE 3

Chemiluminescent Strip Sensor Capable of Measuring C-Reactive Protein (CRP) in Human Serum by Single Sample Injection (Not-Including Conjugation Pad)

Figure 7:
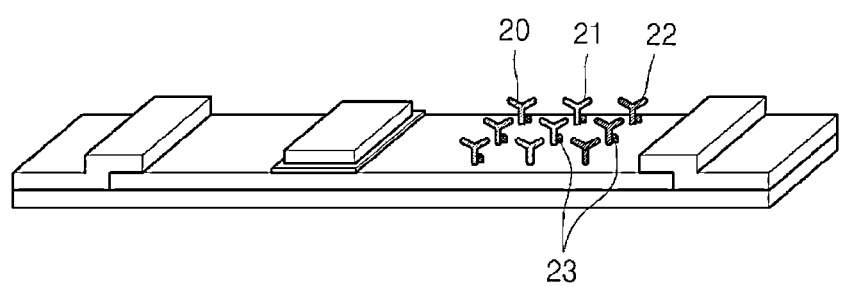
FIG. 7 shows a configuration of a chemiluminescent membrane sensor in Example 3.

As shown in FIG. 7, the conjugation pad was not included, and in order to more increase availability of the chemiluminescent immune strip, 0.04 µg of an anti-CRP antibody-peroxidase complex was pre-treated with 100 µg of Surfactant 10G and 200 µg of PVP 55K, and treated in the reaction membrane at the front side of the reactant storing part. In addition, 140 µg of luminol, 58 µg of choline chloride, and 1.15 µg of p-coumaric acid as a luminescent reaction amplifier were treated in the reactant storing part.

Figure 8:
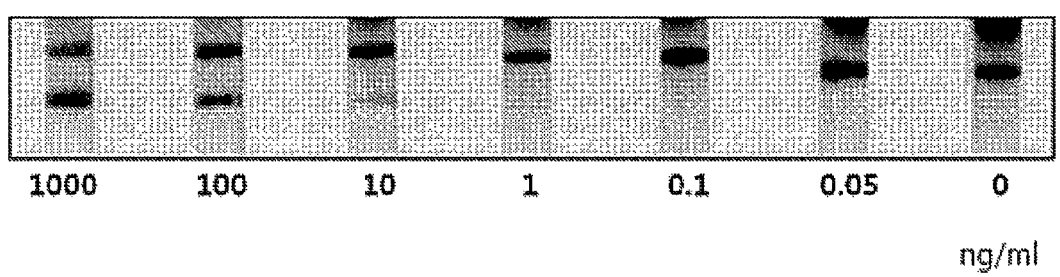
FIG. 8 is a photograph showing results measured for a concentration of C-reactive protein (CRP) in a human serum in Example 3.

90 µL of the serum was injected into the sample pad as the same as Example 3, and the luminol luminescent reaction was confirmed, and a picture measured depending on a concentration of CRP in the injected serum was shown in FIG. 8. It was confirmed from FIG. 8 that the detection was achieved up to a concentration of about 50 pg/ml.

Figure 9:
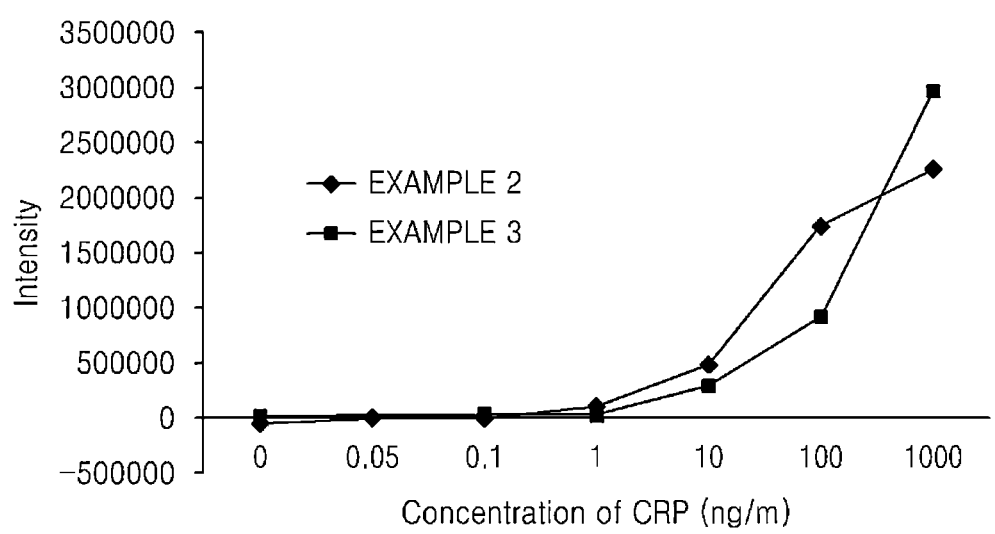
FIG. 9 is a graph showing comparison of a luminescence degree for each concentration of CRP in a human serum between Examples 2 and 3 measured by a luminescence tester.

Meanwhile, a luminescent degree of Examples 2 and 3 was measured using a luminescent image analyzer (LAS-3000, FUJI PHOTO FILM CO., LTD) and results thereof were shown in FIG. 9.

It was confirmed from FIG. 9 that a luminescent degree was increased depending on a concentration of CRP in the serum through Examples 2 and 3 above, such that a precise biosensing process was capable of being achieved.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

The invention claimed is:

1. A membrane strip biosensor using a lateral flow, the biosensor comprising:
   a reaction membrane configured to facilitate a liquid sample to flow through the reaction membrane:
   an asymmetric membrane on the reaction membrane, and having an asymmetrical shape comprising:
   a first portion comprising a plurality of first pores; and
   a second portion between the first portion and the reaction membrane, the second portion comprising a plurality of second pores,
   wherein an average pore size of the first pores is greater than an average pore size of the second pores;
   a reactant storing part on the asymmetric membrane, and configured to store a treated reactant,
   a sample pad at one end of the reaction membrane; and
   an absorption pad at an other end of the reaction membrane,
   wherein the asymmetric membrane is configured to transfer the treated reactant to the reaction membrane.

2. The membrane strip biosensor of claim 1, wherein pores includes in the asymmetric membrane have an average pore size of 0.01 to 50 µm.

3. The membrane strip biosensor of claim 1, wherein the asymmetric membrane comprises one or more kinds selected from polysulfone, polyethersulfone and polycarbonate.

4. The membrane strip biosensor of claim 1, wherein the reaction membrane comprises one or more kinds selected from nitrocellulose, nylon, polysulfone, polyethersulfone, and polyvinylidene fluoride (PVDF).

5. The membrane strip biosensor of claim 1, further comprising a conjugation pad positioned so as to be adjacent to the sample pad.

6. The membrane strip biosensor of claim 5, wherein the conjugation pad is configured to store a first reactant that reacts with an analysis target material in the liquid sample, and the treated reactant in the reactant storing part comprises a second reactant that generates a signal.

7. A method for analyzing a bio sample comprising:
   measuring an analysis target material by injecting the sample into the membrane strip biosensor of claim 1.

8. The membrane strip biosensor of claim 6, wherein the first reactant comprises one or two or more kinds of conjugates selected from antibodies, antigens, enzymes, peptides, proteins, DNAs, RNAs, peptide nucleic acids (PNAs), aptamers and nanoparticles.

9. The membrane strip biosensor of claim 6, wherein the second reactant comprises one or more kinds selected from light absorbing materials, fluorescent materials, luminescent materials, electrochemical signal generating materials and signal amplifying materials amplifying intensity of light absorption signal, fluorescent signal, luminescent signal and electrochemical signal.

10. The membrane strip biosensor of claim 5, further comprising:
    a lower substrate below the reaction, membrane,
    wherein each of the sample pad, the absorption pad, and the conjugation pad is stair shaped, having a first bottom surface, a second bottom surface, a first top surface, and a second top surface,
    wherein the first bottom surface of the sample pad is attached to the lower substrate,
    wherein the second bottom surface of the sample pad is attached to the first top surface of the conjugation pad,
    wherein the first bottom surface of the conjugation pad is attached to the lower substrate,
    wherein the second bottom surface of the conjugation pad is attached to the top of the reaction membrane,
    wherein the first bottom surface of the absorption pad is attached to the lower substrate, and
    wherein the second bottom surface of the absorption pad is attached to the top of the reaction membrane.

11. The membrane strip biosensor of claim 1, wherein the asymmetric membrane comprises polycarbonate.

12. The membrane strip biosensor of claim 1, wherein the asymmetric membrane comprises polyethersulfone.

13. The membrane strip biosensor of claim 1, wherein the reaction membrane comprises polyvinylidene fluoride (PVDF).

14. A membrane strip biosensor using a lateral flow, the biosensor comprising:
   a reaction membrane configured to enable a liquid sample to laterally flow;
   a lower substrate under the reaction membrane,
   an asymmetric membrane on the reaction membrane, and having an asymmetrical shape comprising:
      a first portion comprising a plurality of first pores; and
      a second portion under the first portion comprising a plurality of second pores,
         wherein an average pore size of the first pores are greater than an average pore size of the second pores;
   a reactant storing part on the first portion of the asymmetric membrane, and configured to store a treated reactant,
   wherein the asymmetric membrane is configured to transfer the treated reactant to the reaction membrane,
   a conjugation pad directly attached to one end of the reaction membrane;
   an absorption pad directly attached to the other end of the reaction membrane; and
   a sample pad on the one end of the reaction membrane upstream of the conjugation pad relative to a direction of a lateral flow,
   wherein each of the sample pad, the absorption pad, and the conjugation pad is stair shaped, having a first bottom surface, a second bottom surface, a first top surface, and a second top surface, wherein
      the first bottom surface of the sample pad is attached to the lower substrate,
      the second bottom surface of the sample pad is directly attached to the first top surface of the conjugation pad,
      the first bottom surface of the conjugation pad is directly attached to the lower substrate,
      the second bottom surface of the conjugation pad is directly attached to the top of the reaction membrane,
      the first bottom surface of the absorption pad is directly attached to the lower substrate, and
      the second bottom surface of the absorption pad is directly attached to the top of the reaction membrane.

15. The membrane strip biosensor of claim 1, wherein at least a part of the reaction membrane between the asymmetric membrane and the absorption pad is configured to store a first reactant that reacts with an analysis target material in the liquid sample and the reactant storing part is configured to store the treated reactant that generates a signal.

16. The membrane strip biosensor of claim 15, wherein the first reactant comprises one or two or more kinds of conjugates selected from antibodies, antigens, enzymes, peptides, proteins, DNAs, RNAs, peptide nucleic acids (PNAs), aptamers and nanoparticles.

17. The membrane strip biosensor of claim 15, wherein the treated reactant comprises one or more kinds selected from light absorbing materials, fluorescent materials, luminescent materials, electrochemical signal generating materials and signal amplifying materials amplifying intensity of light absorption signal, fluorescent signal, luminescent signal and electrochemical signal.

* * * * *